United States Patent [19]

Barnard et al.

[11] Patent Number: 5,519,155

[45] Date of Patent: May 21, 1996

[54] PLATINUM COMPLEXES

[75] Inventors: Christopher F. J. Barnard, Reading, United Kingdom; Gerald E. Bossard, King of Prussia, Pa.

[73] Assignee: Johnson Matthey Public Limited Company, London, England

[21] Appl. No.: 428,444

[22] Filed: Apr. 25, 1995

[30] Foreign Application Priority Data

Apr. 26, 1994 [GB] United Kingdom ............. 9408218

[51] Int. Cl.$^6$ .................... C07F 15/00; A61K 31/28
[52] U.S. Cl. .................................................. 556/137
[58] Field of Search ..................... 556/137; 514/492

[56] References Cited

PUBLICATIONS

Chemical Abstracts 111:208703z (1989).
Chemical Abstracts 103:152569a (1985).
Chemical Abstracts 101:182625s (1984).

Primary Examiner—Porfirio Nazario-Gonzales
Attorney, Agent, or Firm—Cushman Darby & Cushman

[57] ABSTRACT

Pt(IV) complexes of formula I,

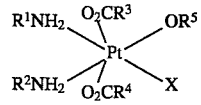

where
  X is halide, pseudohalide or OH,
  $R^1$ and $R^2$ are H, $C_1$ to $C_6$ alkyl, cycloalkyl, aryl or $R^1NH_2$ is a heterocyclic hydrogen donor, and may be the same or different,
  $R^3$ and $R^4$ are H, $C_1$ to $C_5$ alkyl, cycloalkyl or aryl and may be the same or different, and
  $R^5$ is H, Me or Et,
have activity in vitro and in vivo against cancer cells.

14 Claims, No Drawings

PLATINUM COMPLEXES

The present invention concerns improvements in platinum complexes more especially it concerns platinum complexes having activity against cancer cells.

The activity of many platinum(II) and platinum(IV) complexes against cancer cells has been disclosed in the patent and academic literature. Despite this activity being first published more than twenty years ago, there are still only two such complexes approved as medicines, and there remains a need for new complexes having significant activity and/or a wider spectrum of activity, or offering alternative chemotherapies.

Our European Application No 0328274 discloses certain Pt(IV) carboxylate complexes. These complexes are indicated for use as orally-administered anti-tumour substances.

We now provide novel dicarboxylate Pt(IV) complexes of general formula I,

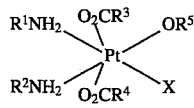

in which

X is a halide atom, especially chlorine, a pseudohalide, for example acetate or hydroxy group, $R^1$ and $R^2$ are hydrogen, $C_1$ to $C_6$ straight or branched chain alkyl or cyclo-alkyl aryl or $R^1NH_2$ is a heterocyclic nitrogen donor, for example pyridine, and $R^1$ and $R^2$ may be the same as or different from one another, $R^3$ and $R^4$ are hydrogen, $C_1$ to $C_5$ straight or branched chain alkyl or cyclo-alkyl or aryl, for example phenyl, and $R^3$ and $R^4$ may be the same as or different from one another, and $R^5$ is hydrogen, methyl or ethyl, and having the cis, trans, cis structure.

In one embodiment, the invention provides synthetic complexes of the general formula I.

The invention further provides a process for the preparation of the complexes of formula I, comprising reacting a complex of formula II,

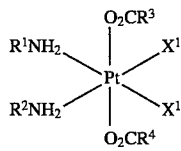

wherein $R^1$ to $R^4$ are as defined above, and $X^1$ is halide or pseudohalide, with a reagent incorporating the group —$OR^5$ in which $R^5$ is as defined above, in the presence of a base.

The complexes of formula II are known and may be prepared as described in EP-A-0328274.

The process may be carried out in a solvent such as water or polar organic solvents such as acetonitrile, dimethylformamide or dimethylacetamide, or mixtures thereof and at a temperature ranging from about room temperature to about 70° C., depending upon the solubility of the reactants. If required, an inert atmosphere may be used.

The complexes of formula I possess activity in standard in vitro and certain in vivo tests which indicate their suitability for the treatment of cancer.

The complexes of the invention may be utilised, according to the invention, as an active component in a pharmaceutical composition comprising a complex of formula I, in admixture with a pharmaceutically acceptable carrier or diluent. The invention also includes the use of complexes of formula I, for the preparation of a medicament for the treatment of cancer.

The active complexes may be administered in the form of pharmaceutical compositions formulated according to well known principles and incorporating the complex, preferably in unit dose form, in combination with a pharmaceutically acceptable diluent or carrier. Such compositions may be in the form of solutions or suspensions for injection, or be in capsule, tablet, dragee, or other solid composition or as a solution or suspension for oral administration, or formulated into pessaries or suppositories, or sustained release form of any of the above. Suitable diluents, carriers, excipients and other components are known. It may be desirable also to formulate a composition for topical administration such as an ointment or cream, or to be administered as a transdermal patch.

The pharmaceutical compositions according to the invention may contain dosages determined in accordance with conventional pharmacological methods, suitably to provide active compounds in the dosage range in humans of from 0.1 to 100 mg/kg body weight per day, in a single unit dose or in a number of smaller unit doses. Preferred dosage ranges are 1 to 30 mg/kg body weight per day.

The complexes of the invention may be administered alone or in combination with another chemotherapeutic agent, such as cisplatin, either as a single treatment or course of treatment or as part of combined therapy with other pharmaceuticals to overcome or diminish side effects or to improve bio-availability, or in combination with other therapies such as radiation treatment.

The invention will now be described by way of example only.

EXAMPLE 1 c,t,c-[PtCl(OMe)(O$_2$CC$_3$H$_7$)$_2$NH$_3$(c-C$_6$H$_{11}$NH$_2$)]

| IR | | | | |
|---|---|---|---|---|
| NMR | $^1$H | Pt—OCH$_3$ | δ2.92 | |
| X-ray diffraction (single crystal) | | | | |
| Elem Analysis | | C | H | N | Cl |
| Theory | | 32.63 | 6.03 | 5.08 | 6.44 |
| Found | | 32.69 | 5.82 | 4.88 | 6.64 |

Synthesis:

A solution of sodium methoxide in methanol (0.1M) was prepared. To this solution (36 ml, 3.6 mmol) was added c,t,c-[PtCl$_2$(O$_2$CC$_3$H$_7$)$_2$NH$_3$(c-C$_6$H$_{11}$NH$_2$)] (2 g, 3.6 mmol). The mixture was stirred at room temperature for 3 days. The precipitate of sodium chloride was removed by filtration and the flitrate evaporated to dryness under reduced pressure. The residue was taken up in absolute ethanol, filtered and re-evaporated twice more. The residual oil crystallised on standing. The solid was collected by filtration, washed with a little ethanol, then diethyl ether and dried in air. The product was finally dried in vacuo. Yield: 0.5 g (25%.)

The complex has also been prepared by reaction of the platinum complex starting material with Cs$_2$CO$_3$ in methanol. This illustrates the principle that the choice of base is not critical for the formulation of the product as the incoming nucleophile is normally provided by the solvent. In the case of weakly coordinating solvents such as dimethylacetamide the base (eg OH$^-$) may then also act as the nucleophile in the formation of the product.

EXAMPLE 2
c,t,c-[Pt(OH)$_2$(OAc)$_2$NH$_3$(c-C$_6$H$_{11}$NH$_2$)]

| | | | | |
|---|---|---|---|---|
| IR | | | | |
| HPLC | | | | |
| Elem Analysis | | C | H | N |
| Theory | | 25.91 | 5.22 | 6.05 |
| Found | | 25.78 | 5.20 | 5.98 |

To a solution of c,t,c-[PtCl$_2$(OAc)$_2$NH$_3$(c-C$_6$H$_{11}$NH$_2$)] (1.31 g 2.62 mmol) in dimethylacetamide (10 ml) was added aqueous sodium hydroxide (1.0M, 5.38 ml, 5.38 mmol). Some of the starting complex precipitated from solution on mixing. The mixture was stirred and heated at 60° C. for three hours. The mixture was allowed to cool and diluted with water (ca 50 ml). The pale yellow precipitate was collected by filtration and washed with water. The product was dried in vacuo. Yield: 0.42 g (35%)

EXAMPLE 3
c,t,c-[PtCl(OH)(O$_2$CC$_5$H$_{11}$)$_2$(i-C$_3$H$_7$NH$_2$)$_2$]

| | | | | | |
|---|---|---|---|---|---|
| IR | | | | | |
| HPLC | | | | | |
| Elem Analysis | | C | H | N | Cl |
| Theory | | 36.27 | 6.94 | 4.70 | 5.96 |
| Found | | 36.47 | 7.18 | 4.73 | 5.59 |

Synthesis:
The complex c,t,c-[PtCl$_2$(O$_2$CC$_5$H$_{11}$)$_2$(i-C$_3$H$_7$NH$_2$)$_2$] (0.5 g, 0.81 mmol was stirred in 50:50 volume % acetonitrile water mixture (ca 100 ml) to give a clear pale yellow solution. Potassium hydroxide solution (1.0M, 0.84 ml, 0.84 mmol) was added. After a few minutes the product began to precipitate from solution. After stirring for 30 minutes at room temperature the solution was filtered and the solid product washed with water. The product was dried in vacuo. Yield: 0.27 g (57%)

EXAMPLE 4 c,t,c-[PtCl(OH)(OAc)$_2$(i-C$_3$H$_7$NH$_2$)$_2$]

| | | | | | |
|---|---|---|---|---|---|
| IR | | | | | |
| HPLC | | | | | |
| Elem Analysis | | C | H | N | Cl |
| Theory | | 24.82 | 5.21 | 5.79 | 7.34 |
| Found | | 25.11 | 4.88 | 5.65 | 7.46 |

Synthesis:
The complex c,t,c-[PtCl$_2$(OAc)$_2$(i-C$_3$H$_7$NH$_2$)$_2$] (0.5 g, 1.0 mmol) was stirred in 50:50 volume % acetonitrile water mixture (ca 20 ml). Potassium hydroxide solution (1.0M, 1.3 ml, 1.3 mmol) was added and the mixture stirred at room temperature. After stirring for 3 hours the solution was evaporated under reduced pressure until the product began to precipitate. The solution was then allowed to stand for ca 1 hour to allow the product to crystallise. The mixture was filtered and the product washed with a little water and dried in vacuo. Yield: 0.19 g (39%).

EXAMPLE 5 c,t,c-[Pt(OH)$_2$(OAc)$_2$(i-C$_3$H$_7$NH$_2$)$_2$]

| Elem Analysis | C | H | N |
|---|---|---|---|
| Theory | 25.81 | 5.63 | 6.02 |
| Found | 25.72 | 5.63 | 6.04 |

Synthesis:
To a solution of tetramethylammonium hydroxide pentahydrate (0.476 g, 2.63 mmol) in acetonitrile (4 ml) was added c,t,c-[PtCl$_2$(OAc)$_2$(i-C$_3$H$_7$NH$_2$)$_2$] (0.66 g, 1.31 mmol). The mixture was shaken for 20 minutes. The starting materials dissolved to give an orange solution from which a pale yellow solid precipitated. The solid was collected by filtration and washed with acetonitrile (60 ml) and then diethyl ether. The product was dried in vacuo. Yield: 0.54 g (89%)

This product was also prepared by treating a solution of c,t,c-[PtCl$_2$(OAc)$_2$(i-C$_3$H$_7$NH$_2$)$_2$] in methanol/water with an excess of AG 1-X8 ion exchange resin in the hydroxide form. After stirring the mixture overnight the resin was removed by filtration. The filtrate was evaporated to dryness under reduced pressure and the residue treated with methanol/diethyl ether. The product solidified and was collected by filtration and dried in vacuo.

EXAMPLE 6
c,t,c-[PtCl(OH)(OAc)$_2$NH$_3$(c-C$_6$H$_{11}$NH$_2$)]

| | | | | | |
|---|---|---|---|---|---|
| IR | | | | | |
| HPLC | | | | | |
| Elem Analysis | | C | H | N | Cl |
| Theory | | 24.92 | 4.81 | 5.82 | 7.37 |
| Example 6 H$_2$O | | 24.02 | 5.05 | 5.61 | 7.11 |
| Found | | 24.13 | 5.00 | 5.52 | 7.35 |

Synthesis:
The complex c,t,c-[PtCl$_2$(OAc)$_2$NH$_3$(c-C$_6$H$_{11}$NH$_2$)] (1.0 g, 2 mmol) was dissolved in 75:25 volume % acetonitrile water mixture (ca 150 ml). Potassium hydroxide solution (1M, 3 ml, 3 mmol) was added and the solution was stirred for 2 hours at room temperature. The solution was evaporated under reduced pressure until the product began to precipitate. The solution was then allowed to stand for 15 minutes to complete crystallisation. The product was collected by filtration and washed with water. The product was dried in vacuo. Yield: 0.32 g (33%)

EXAMPLE 7
c,t,c-[Pt(OH)(OMe)(OAc)$_2$(i—C$_3$H$_7$NH$_2$)$_2$]

| | | | | |
|---|---|---|---|---|
| IR | | | | |
| NMR | $^1$H | Pt—OCH$_3$ | | δ2.84 |
| Elem Analysis | | C | H | N |
| Theory | | 27.56 | 5.89 | 5.84 |
| Found | | 28.16 | 6.00 | 5.76 |

Synthesis:
The complex c,t,c-[PtCl$_2$(OAc)$_2$(i-C$_3$H$_7$NH$_2$)$_2$] (0.5 g, 1 mmol) was suspended in dry methanol and sodium methoxide in methanol (25% solution, 0.43 g, 2 mmol) was added dropwise. All solids dissolved and the mixture was stirred at room temperature for 16 hours under nitrogen. The solvent was removed by evaporation under reduced pressure and the residue taken up in dichloromethane. The mixture was filtered to remove sodium chloride and addition of diethyl ether to the filter gave a yellow solid. This solid was re-crystallised from methanol/ethyl acetate. (During the course of the synthesis reaction with atmospheric moisture leads to conversion of the di-methoxo-complex to the monomethoxo-mono-hydroxo product.) Yield: 0.28 g (60%)

In vitro biological testing was conducted using cell lines derived from human ovarian carcinomas and maintained at the Institute of Cancer Research, Sutton, England (see C A Hills and colleagues, Br J Cancer 59, 527–534 (1989)). Monolayer cells were trypsinized and seeded in 96-well microtiter plates at a density of 1×10⁴ cells/well in 200 μl of growth medium. Cells were incubated overnight and test compounds were added to triplicate wells at various concentrations for a total of 48 to 96 hours. For toxicity analysis after drug exposure, the cells were fixed with trichloroacetic acid and stained for cellular protein content by incubation for 30 minutes with 0.4% (wt/vol) sulphorhodamine B (SRB) dissolved in 1% acetic acid. The unbound dye was removed by 1% acetic acid washes, and the bound dye was extracted with 10 mM Tris buffer. The amount of dye in solution was quantified by absorbance at 564 nm. Table 1 gives $IC_{50}$ results in μM.

TABLE 1

| Compound | HX-62 | SKOV-3 | 41M | 41M$^R$ | CH1 | CH$^R$ | A2780 | A2780$^R$ |
|---|---|---|---|---|---|---|---|---|
| Example 1 | 0.22 | 0.03 | 0.01 | 0.013 | 0.002 | NA | NA | NA |
| 2 | 37 | 21 | 6.5 | 4.3 | 0.74 | 1.35 | 4.2 | 3.7 |
| 3 | 0.05 | 0.0046 | <0.0025 | <0.0025 | <0.0025 | <0.0025 | <0.0025 | 0.0029 |
| 4 | 2.1 | 1.6 | 0.89 | 0.59 | 0.086 | 0.21 | 0.65 | 1.9 |
| 6 | 3.1 | 1.15 | 0.24 | 0.44 | 0.022 | 0.082 | 0.31 | 0.93 |
| 7 | 12.5 | 6.1 | 3.1 | 2.5 | 0.26 | NA | NA | NA |

NA = data not available

The compounds of the invention were then tested in vivo in mice having Adj/PC6 tumours. The Adj/PC6 testing was carried out as described by P M Goddard et al presented in Sixth NCI-EORTC Symposium on New Drugs in Cancer Therapy 1989, which is a development of the basic method described by T A Connors et al, Chem Biol Interact 5,415 (1972). The animals were sacrificed when moribund. The compounds were administered parenterally (ip) or orally (po), or in the case of the Example 2 compound, iv at doses of 2.5, 5, 10 and 20 mg/kg (4 animals per dose group).

In the testing, $LD_{50}$ and $ED_{90}$ values in mg/kg body weight were determined in the conventional manner. The therapeutic index (TI) was calculated as the ratio of $LD_{50}$ to $ED_{90}$, and the results are shown below.

TABLE 2

| | i.p. | | | p.o. | | | i.v. | | |
|---|---|---|---|---|---|---|---|---|---|
| Compound | $LD_{50}$ | $ED_{90}$ | TI | $LD_{50}$ | $ED_{90}$ | TI | $LD_{50}$ | $ED_{90}$ | TI |
| Example 1 | 17.5 | 2.6 | 6.7 | | | | | | |
| Example 2 | 17.5 | 4.2 | 4.2 | 670 | 42 | 16 | 14 | <2.5 | >5.6 |

The in vitro and in vivo testing results indicate that the complexes of the invention possess useful activity against cancer cells. The greater therapeutic index for the product of Example 2 when given by the oral route compared to parenteral administration indicates the potential for oral administration.

We claim:

1. A Pt(IV) complex of general formula I,

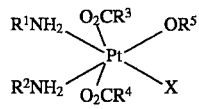

in which

X is a halide atom, a pseudohalide, or hydroxy group, $R^1$ and $R^2$ are hydrogen, $C_1$ to $C_6$ straight or branched chain alkyl or cyclo-alkyl, aryl or $R^1NH_2$ is a heterocyclic nitrogen donor, and $R^1$ and $R^2$ may be the same as or different from one another, $R^3$ and $R^4$ are hydrogen, $C_1$ to $C_5$ straight or branched chain alkyl or cyclo-alkyl or aryl, and $R^3$ and $R^4$ may be the same as or different from one another, and p1 $R^5$ is hydrogen, methyl or ethyl, and having the cis, trans, cis structure.

2. A complex according to claim 1, wherein X is chloro or hydroxy and one of $R^1$ and $R^2$ is hydrogen.

3. A complex according to claim 1, wherein $R^3$ and $R^4$ are methyl.

4. Complex of claim 1 which c,t,c— [PtCl(OMe)(O$_2$CC$_3$H$_7$)$_2$NH$_3$(c—C$_6$H$_{11}$NH$_2$)].

5. Complex of claim 1 which is c,t,c— [Pt(OH)$_2$(OAc)$_2$NH$_3$(c—C$_6$H$_{11}$NH$_2$)].

6. Complex of claim 1 which is c,t,c— [PtCl(OH)(O$_2$CC$_5$H$_{11}$)$_2$(i—C$_3$H$_7$NH$_2$)$_2$].

7. Complex of claim 1 which is c,t,c— [PtCl(OH)(OAc)$_2$(i—C$_3$H$_7$NH$_2$)$_2$].

8. Complex of claim 1 which is c,t,c— [PtCl(OH)(OAc)$_2$NH$_3$(c—C$_6$H$_{11}$NH$_2$)].

9. Complex of claim 1 which is c,t,c— [Pt(OH)(OMe)(OAc)$_2$(i—C$_3$H$_7$NH$_2$)].

10. A process for the preparation of a complex according to claim 1, comprising reacting a complex of formula II,

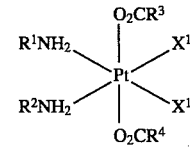

wherein $R^1$ to $R^4$ are as defined above, and $X^1$ is halide or pseudohalide, with a reagent incorporating the group —OR$^5$ in which $R^5$ is as defined above, in the presence of a base.

11. A pharmaceutical composition for the treatment of cancer cells, comprising as an active component, a complex according to claim 1 in admixture with a pharmaceutically acceptable carrier or diluent.

12. A complex according to claim 1 wherein X is chlorine or acetate.

13. A complex according to claim 1 wherein $R^1NH_2$ is pyridine.

14. A complex according to claim 1 wherein the aryl for $R^3$ or $R^4$ is phenyl.

* * * * *